United States Patent [19]

Suyama et al.

[11] Patent Number: 5,117,047
[45] Date of Patent: May 26, 1992

[54] PEROXY ESTER

[75] Inventors: Shuji Suyama; Mitsukuni Katoh; Tooru Nishikawa, all of Aichi, Japan

[73] Assignee: Nippon Oil & Fats Co., Ltd., Tokyo, Japan

[21] Appl. No.: 765,208

[22] Filed: Sep. 25, 1991

[30] Foreign Application Priority Data

Sep. 28, 1990 [JP] Japan ................................. 2-257633
Oct. 25, 1990 [JP] Japan ................................. 2-285801
Dec. 21, 1990 [JP] Japan ................................. 2-412711

[51] Int. Cl.⁵ .......................................... C07C 331/00
[52] U.S. Cl. ................................................. 560/302
[58] Field of Search ....................................... 560/302

[56] References Cited

U.S. PATENT DOCUMENTS 3,869,489  3/1975  Tiquet et al. ........................ 560/302

Primary Examiner—Mary C. Lee
Assistant Examiner—Robert C. Whittenbaugh
Attorney, Agent, or Firm—Oblon, Spivak, McClelland, Maier & Neustadt

[57] ABSTRACT

A 1-cyclohexyl-1-methylethyl peroxy ester, a novel compound, represented by the formula:

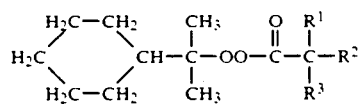

wherein $R^1$ stands for one member selected from the group consisting of H and alkyl groups and $R^2$ and $R^3$ independently stand for an alkyl group, provided that $R^2$ and $R^3$ each stand for an alkyl group of 1 to 5 carbon atoms and the sum of the carbon atoms of $R^2$ and $R^3$ is in the range of from 2 to 6 where $R^1$ is H and $R^1$, $R^2$, and $R^3$ each stand for an alkyl group of 1 to 9 carbon atoms and the sum of the carbon atoms of $R^1$, $R^2$, and $R^3$ is in the range of from 3 to 11 where $R^1$ is an alkyl group, a polymerization initiator for a vinyl group-containing compound monomer and a curing agent for an unsaturated polyester resin, which polymerization initiator and curing agent both contain as an active component thereof the ester mentioned above.

5 Claims, No Drawings

PEROXY ESTER

BACKGROUND OF THE INVENTION

1. Field of the Invention

This invention relates to novel peroxy esters, specifically 1-cyclohexyl-1-methylethyl peroxy esters, polymerization initiators having the peroxy esters as a principal component and used for vinyl monomers such as, for example, (meth)acrylic esters, methyl methacrylate, vinyl chloride and vinyl acetate, and curing agents having the peroxy esters as a principal component and used for unsaturated polyester resins.

2. Prior Art Statement

Heretofore, methods for using various organic peroxides and azo compounds such as azo-isobutyronitrile ("AIBN") as polymerization initiators for vinyl monomers either alone or in combination with copolymerizable vinyl monomers or as curing agents for unsaturated polyester resins have been known to the art.

As initiators of low-temperature polymerization of such a monomer as vinyl chloride or a derivative thereof, for example, the peroxy esters such as cumyl peroxy neodecanoate (CND) and paramenthane peroxy neodecanoate (PMND) whose carboxylic acid moiety has a tertiary α-carbon are disclosed in Japanese Patent Public Disclosure SHO 58(1983)-120611. As polymerization initiators in the polymerization of unsaturated monomers such as styrene and methyl methacrylate or in the copolymerization of these unsaturated monomers in combination with other copolymerizable unsaturated monomers and as curing agents for unsaturated polyester resins, benzoyl peroxide (BPO), t-butylperoxy-2-ethyl hexanoate (t-BO), pinane peroxy-2-ethyl hexanoate (PEO), or paramenthane peroxy-2-ethyl hexanoate (PMO) has been used either alone or in combination with a peroxide which is active at a higher temperature. AIBN has been used as a polymerization initiator for vinyl acetate.

The method for polymerizing a monomer such as vinyl chloride or a derivative thereof by the use of CND and PMND as a polymerization initiator, however, imparts the produced polymer with the offensive odor of the polymerization initiator itself or the decomposition product thereof. The polymerization of styrene or methyl methacrylate and the curing of an unsaturated polyester resin by the use of BPO, t-BO, PEO, or PMO are inferior in productivity due to slow polymerizing and curing speeds and low in quality due to impregnation of the polymer or cured product with the offensive odor. The polymerization of vinyl acetate by the use of AIBN causes undesirable coloration of the produced polymer. There is thus a need for a polymerization initiator and a curing agent which produce high polymerizing and curing speeds and yield a polymer and a cured product which are not imparted with unwanted odor or color. The present invention aims to meet this need.

SUMMARY OF THE INVENTION

The present invention relates to a 1-cyclohexyl-1-methylethyl peroxy esters, a novel compound not yet published in the literature, represented by the formula:

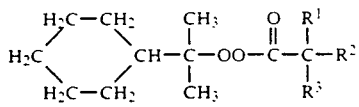

(wherein R¹ stands for one member selected from the group consisting of H and alkyl groups and R² and R³ independently stand for an alkyl group, provided that R² and R³ independently stand for an alkyl group of one to five carbon atoms the sum of the carbon atoms of R² and R³ is in the range of from 2 to 6 where R¹ is H, and R¹, R², and R³ independently stand for an alkyl group of one to nine carbon atoms and the sum of the carbon atoms of R¹, R², and R³ is in the range of from 3 to 11 where R¹ is an alkyl group, and a polymerization initiator for a vinyl monomer and a curing agent for an unsaturated polyester resin which have the peroxy ester mentioned above as an active component thereof.

DESCRIPTION OF THE PREFERRED EMBODIMENTS

The peroxy ester of the present invention can be produced in accordance with the conventional method as follows. Specifically, the peroxy ester can be synthesized by the reaction of a carboxylic acid chloride with 1-cyclohexyl-1-methylethyl hydroperoxide in the presence of an alkali. The alkalis which are effectively usable for the reaction mentioned above include inorganic bases such as potassium hydroxide and sodium hydroxide, water solutions of these inorganic bases, and amines such as pyridine, for example. When the synthesis is carried out in the presence of a solvent such as benzene, n-hexane, or dioxane, the reaction time for synthesis becomes shorter and the yield of the synthesis improves. The reaction temperature is approximately in the range of from −10° C. to 30° C.

The carboxylic acid chloride to be used in the production of the peroxy ester of the present invention can be produced by the reaction of carboxylic acid with a suitable chlorinating agent such as phosphorus trichloride, phosphorus oxytrichloride, or thionyl chloride and then isolating an acid chloride from the resultant reaction mixture. The carboxylic acids which are usable herein include iso-butyric acid, pivalic acid, neo-hexanoic acid, neo-nonanoic acid, 2-ethylhexanoic acid, neo-decanoic acid, and neo-tridecanoic acid, for example. The 1-cyclohexyl-1-methylethyl hydroperoxide to be used in the production of the peroxy ester of the present invention can be produced by causing hexahydro-α-cumyl alcohol to react with an excess of hydrogen peroxide in the presence of a strong acid catalyst such as sulfuric acid, phosphoric acid, perchloric acid, p-toluenesulfonic acid, or a strong acid type ion-exchange resin.

Specific examples of the peroxy ester of the present invention include 1-cyclohexyl-1-methylethyl peroxyisobutyrate, 1-cyclohexyl-1-methylethyl peroxy octoate, 1-cyclohexyl-1-methylethyl peroxy pivalate, 1-cyclohexyl-1-methylethyl peroxy neo-hexanoate, 1-cyclohexyl-1-methylethyl peroxy neo-decanoate, and 1-cyclohexyl-1-methylethyl peroxy neo-tridecanoate. The peroxy esters of the present invention can be identified by the following method.

The infrared absorption spectrum (IR spectrum) allows confirmation of the C═O bond and the O—O bond and the nucleus magnetic resonance spectrum (NMR spectrum) reveals the structures of $CH_3$, $CH_2$, and CH and they jointly enable determination of the overall chemical structure. Further, the peroxide group content can be ascertained by using iodometry to determine active oxygen.

The peroxy ester of the present invention is useful as a polymerization initiator and a curing agent. The peroxy ester, when used as a polymerization initiator, accelerates the polymerization rate and improves the productivity. To be more specific, the peroxy ester of the present invention is useful as a polymerization initiator for such unsaturated monomers as vinyl chloride, styrene, methyl methacrylate, and vinyl acetate and for copolymerization of these unsaturated monomers with other copolymerizable unsaturated monomers such as butadiene, acrylonitrile, maleic anhydride, α-methyl styrene, and acrylic esters. The particular peroxy ester of the present invention to be used for the polymerization of a vinyl monomer is suitably selected, depending on the kind of the vinyl monomer and the polymerization temperature thereof. For the polymerization of a vinyl chloride monomer which has a polymerization temperature approximately in the range of from 40° C. to 50° C., 1-cyclohexyl-1-methylethyl peroxy neodecanoate, for example, functions particularly desirably. For the polymerization of methyl methacrylate or derivative thereof having a polymerization temperature approximately in the range of from 70° C. to 90° C., 1-cyclohexyl-1-methylethyl peroxy octoate functions, for example, particularly desirably. For the polymerization of styrene or a derivative thereof having a polymerization temperature approximately in the range of from 90° C. to 110° C., 1-cyclohexyl-1-methylethyl peroxy isobutyrate, for example, functions particularly desirably. For the polymerization of vinyl acetate or a derivative thereof and methyl methacrylate or a derivative thereof which have polymerization temperatures approximately in the range of from 60° C. to 70° C., 1-cyclohexyl-1-methylethyl peroxy pivalate, for example, functions particularly desirably. Further, the peroxy ester of the present invention is also useful as a curing agent for unsaturated polyester resins. Particularly, 1-cyclohexyl-1-methylethyl peroxy-secondary aliphatic esters of the present invention, in a range of medium to high curing temperatures (approximately from 70° C. to 100° C.), effect desired curing at a high speed, yield cured products having neither offensive odor nor unwanted color, and provide cured products of high quality with high production efficiency. When the peroxy ester of the present invention is used as a polymerization initiator or a curing agent as described above, it may be used either alone or in combination with one or more other peroxides. The peroxide thus used additionally varies depending on the polymerizing or curing speed. Where the temperature is not higher than about 80° C., at least one member selected from the group consisting of peroxy esters, diacyl peroxides, and peroxy dicarbonates which have a 10-hour half-life temperature ($T_{10}$) in the range of from 30° C. to 65° C. is used. To be specific, usable peroxy esters include t-butyl peroxy pivalate (55° C.), t-butyl peroxy neo-decanoate (46.5° C.), and cumyl peroxy neo-decanoate (36.6° C.), for example, usable diacyl peroxides include isobutylyl peroxide (32.5° C.), 3,5,5-trimethylhexanoyl peroxide (59.5° C.), lauroyl peroxide (62° C.), and octanoyl peroxide (62° C.), for example, and usable peroxy dicarbonates include di(2-ethylhexyl) peroxy dicarbonate (43.4° C.), di-n-propyl peroxy dicarbonate (40.5° C.), and diisopropyl peroxy dicarbonate (40.5° C.), for example. Peroxides whose $T_{10}$ temperatures are in the range of from 80° C. to 110° C. are used where the polymerizing or curing temperatures above 80° C. Specific peroxides answering this description include 1,1-bis(t-butylperoxy)-3,3,5-trimethyl cyclohexane (90° C.), 1,1-bis(t-butylperoxy)-cyclohexane (91° C.), t-butyl peroxyisopropyl carbonate (98° C.), and t-butyl peroxybenzoate (104° C.), for example.

The amount of the polymerization initiator to be used in the present invention generally is in the range of from 0.001 to 1 part by weight as pure substance, preferably from 0.01 to 0.5 part by weight, based on 100 parts by weight of the vinyl monomer being used. If this amount is less than 0.001 part by weight, the polymerization rate is liable to be unduly slow. If the amount exceeds 1 part by weight, the disadvantage arises that the reaction of polymerization is difficult to control and the produced polymer is liable to acquire inferior physical properties. The amount of the curing agent to be used in the present invention is generally in the range of from 0.05 to 3 parts by weight as pure substance, preferably from 0.5 to 1 part by weight, based on 100 parts by weight of the unsaturated polyester resin to be cured. If this amount is less than 0.05 part by weight, the curing speed is slow, the curing does not proceed to its completion, and the produced cured substance lacks usefulness. Conversely, if this amount exceeds 3 parts by weight, the curing speed becomes too fast so that the cured substance sustains cracks and is consequently of poor quality. Though the amount of the peroxide to be additionally used for polymerization or curing may be suitably selected, it is generally in the range of from ¼ to 4 times the amount of the 1-cyclohexyl-1-methylethyl peroxy ester to be used. In the polymerization or curing by the use of the peroxy ester of the present invention, a chain transfer agent such as, for example, a mercaptan, an α-methylstyrene dimer, or terpinolene may be used for the purpose of adjusting the polymerizing or curing speed or adjusting the molecular weight. The polymerization of a vinyl monomer by the use of the polymerization initiator of the present invention may be performed by the method of suspension polymerization, bulk polymerization or emulsion polymerization. The curing of an unsaturated polyester resin by the use of the curing agent of the present invention may be carried out by the method of casting or superposition. The temperature of the polymerization of a vinyl monomer or of the curing of an unsaturated polyester resin by the use of the polymerization initiator or the curing agent of this invention is generally in the range of from 30° C. to 120° C. The operation of polymerization or curing may be performed at a fixed temperature or at a gradually elevated temperature in the range of from 30° C. to 120° C. If the polymerizing or curing temperature is below 30° C., the polymerizing or curing time is liable to be unduly long. Conversely, if this temperature exceeds 120° C., the polymerization initiator or the curing agent possesses only a short service life and it is difficult to realize high conversion in the operation of polymerization or curing.

Now, the present invention will be described more specifically below with reference to working examples and comparative experiments.

EXAMPLE 1

[Synthesis of 1-cyclohexyl-1-methylethyl peroxy isobutyrate (C-isobutyrate)]

In a four-neck flask having an inner volume of 1 liter and provided with a stirrer and a thermometer, 336.7 g (1.2 mols) of an aqueous 20% potassium hydroxide solution and 179.4 g (1.1 mols) of 1-cyclohexyl-1-methylethyl hydroperoxide (CMEH) having a purity of 97% were stirred while being kept at an internal temperature of from 10° C. to 15° C. by an external ice bath and 106.6 g (1.0 mol) of isobutyric acid chloride was added dropwise thereto over a period of 30 minutes. Thereafter, the ensuing reaction was continued at 15° C. to 20° C. for two hours. The stirring was discontinued. The contents of the flask were transferred into a separation funnel for phase separation. The organic layer consequently formed was washed twice with 300 g of an aqueous 5% sodium hydroxide solution then washed with water until it was neutralized and finally dried with anhydrous magnesium sulfate. Consequently, 202 g of a liquid product was obtained.

When this liquid product was tested by iodometry, the active oxygen content was found to be 6.92%, the purity of the product to be 98.7%, and the yield of polymerization to be 87.3%.

This liquid product showed the following characteristic properties.

IR: O—O stretching vibration 855 cm$^{-1}$ C=O stretching vibration 1,780 cm$^{-1}$ NMR (CDCl$_3$): 1.08 to 1.16, m, 5H H (a), 1.18, s, 6H H (b), 1.40 to 1.77, m, 6H H (c), 1.61, d, 6H H (d), 4.85 to 5.17, m, 1H H (e).

From the data, the product was confirmed to be an organic peroxide possessing the following chemical structure.

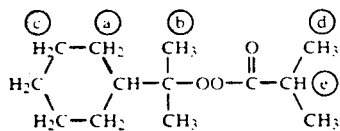

EXAMPLE 2

[Synthesis of 1-cyclohexyl-1-methylethyl peroxy octoate (C-octoate)]

A liquid product was obtained in the amount of 246 g by following the procedure of Example 1, except that 162.7 g (1.0 mol) of 2-ethylhexanoic acid chloride was used in place of isobutyric acid chloride.

When this liquid product was tested by iodometry, the active oxygen content was found to be 5.55%, the purity of the product to be 98.6%, and the yield of polymerization to be 85.3%.

This liquid product showed the following characteristic properties.

IR: O—O stretching vibration 860 cm$^{-1}$ C=O stretching vibration 1,770 cm$^{-1}$ NMR (CDCl$_3$): 0.75 to 0.95, m, 6H H (a), 1.02 to 1.14, m, 5H H (b), 1.20, s, 6H H (c), 1.18 to 1.85, m, 8H H (d), 1.37 to 1.75, m, 6H H (e), 2.21 to 2.23, m, 1H H (f).

From the data, the product was confirmed to be an organic peroxide possessing the following chemical structure.

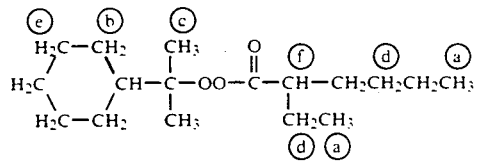

EXAMPLE 3

[Synthesis of 1-cyclohexyl-1-methylethyl peroxy neo-decanoate (C-neodecanoate)]

In a four-neck flask having an inner volume of 200 ml and provided with a stirrer, 28.3 g of an aqueous 35% potassium hydroxide solution was placed and kept stirred at a liquid temperature of 20° C. and a mixture of 17.9 g of 95% 1-cyclohexyl-1-methylethyl hydroperoxide with 10 g of hexane was added thereto. The resultant mixture was further kept stirred at a liquid temperature of 20° C. and 19.1 g of neo-decanoic acid chloride was added dropwise thereto over a period of 10 minutes. The resultant mixture was kept stirred at a liquid temperature of 20° C. for three hours and subsequently stirred with 20 g of cold water added thereto over five minutes. The resultant mixture was subjected to phase separation and then deprived of the aqueous phase. The residual phase was washed with 20 g of an aqueous 5% sodium hydroxide solution and then washed three times with water. The resultant solution was dried over anhydrous magnesium sulfate and left standing under a vacuum to expel the remaining hexane. Consequently, 24.1 g of a colorless liquid product was obtained. The active oxygen content was found to be 4.83%, the purity of the product to be 94.3%, and the yield of polymerization to be 73 mol%.

This substance was identified from the IR and NMR spectra. The results are shown in Table 1. It was further tested for speed of thermal decomposition with benzene as a solvent (concentration: 0.1 mol/liter). As a result, the 10-hour half-life temperature (T$_{10}$) of this peroxy ester was found to be 41.4° C.

EXAMPLE 4

[Synthesis of 1-cyclohexyl-1-methylethyl peroxy pivalate (C-pivalate)]

A colorless liquid product, C-pivalate, was synthesized by following the procedure of Example 3, except that pivalic acid chloride was used instead as a carboxylic acid chloride. The produced substance was identified from the IR and NMR spectra. The results are shown in Table 1.

This substance was tested for speed of thermal decomposition in the same manner as in Example 3. As a result, the 10-hour half-life temperature of this peroxy ester was found to be 49.1° C.

EXAMPLE 5

[Synthesis of 1-cyclohexyl-1-methylethyl peroxy neo-hexanoate (C-neo-hexanoate)]

A colorless liquid C-neo-hexanoate was synthesized by following the procedure of Example 3, except that neo-hexanoic acid chloride was used instead as a carboxylic acid chloride. This substance was identified from the IR and NMR spectra. The results are shown in Table 1.

This substance was tested for speed of thermal decomposition in the same manner as in Example 3. As a result, the 10-hour half-life temperature of this peroxy ester was found to be 46.2° C.

EXAMPLE 6

[Synthesis of 1-cyclohexyl-1-methylethyl peroxy neo-nonanoate)]

A colorless liquid C-neo-nonanoate was synthesized by following the procedure of Example 3, except that neo-nonanoic acid chloride obtained by chlorinating neo-nonanoic acid (produced by Idemitsu Petro-Chemical Co., Ltd. and marketed as "Equacid 9") was used instead as a carboxylic acid chloride. The results are shown in Table 1.

This substance was tested for speed of thermal decomposition in the same manner as in Example 3. As a result, the 10-hour half-life temperature of this peroxy ester was found to be 40.5° C.

EXAMPLE 7

[Synthesis of 1-cyclohexyl-1-methylethyl peroxy neo-tridecanoate(C-neo-tridecanoate)]

A colorless liquid C-neo-tridecanoate was synthesized by following the procedure of Example 3, except that neo-tridecanoic acid chloride obtained by chlorinating neo-tridecanoic acid (produced by Idemitsu Petro-Chemical Co., Ltd. and marketed as "Equacid 13") was used instead as a carboxylic acid chloride. The results are shown in Table 1.

This substance was tested for speed of thermal decomposition in the same manner as in Example 3. As a result, the 10-hour half-life temperature of this peroxy ester was found to be 40.9° C.

From the results, it is clear that the 1-cyclohexyl-1-methylethyl peroxy neo-alkanoates of the present invention have shorter decomposition half lines than t-alkylper acid esters of the prior art derived from the same carboxylic acids.

TABLE 1

| Example | Constitutional formula | Active oxygen (%) | Purity (%) | Yield (%) | IR $\nu_{C=O}$ (cm$^{-1}$) | $^1$H NMR (CDCl$_3$) | $T_{10}$ (°C) |
|---|---|---|---|---|---|---|---|
| 3 | (cyclohexyl)-CH(CH$_3$)-OO-C(=O)-t-C$_9$H$_{19}$ (a); groups (d)(b)(c) | 4.83 | 94 | 73 | 1770 | H(a): δ 0.70~1.60, m, 19H; H(b): δ 0.90~1.33, m, 5H; H(c): δ 1.17, s, 6H; H(d): δ 1.50~1.88, m, 6H | 41.4 |
| 4 | (cyclohexyl)-CH(CH$_3$)-OO-C(CH$_3$)(CH$_3$)-C(=O)-CH$_3$ (a); groups (d)(b)(c) | 6.21 | 94 | 80 | 1765 | H(a): δ 1.04, s, 9H; H(b): δ 0.83~1.33, m, 5H; H(c): δ 1.15, s, 6H; H(d): δ 1.49~1.88, m, 6H | 49.1 |
| 5 | (cyclohexyl)-CH(CH$_3$)-OO-C(=O)-C(CH$_3$)(CH$_3$(c))-CH$_2$-CH$_3$ (a); groups (f)(d)(e)(b) | 5.80 | 93 | 78 | 1765 | H(a): δ 0.75, t, 3H; H(b): δ 1.08, s, 6H; H(c): δ 1.50, q, 2H; H(d): δ 0.88~1.35, m, 5H; H(e): δ 1.18, s, 6H; H(f): δ 1.53~1.90, m, 6H | 46.2 |
| 6 | (cyclohexyl)-CH(CH$_3$)-OO-C(=O)-t-C$_8$H$_{17}$ (a); groups (d)(b)(c) | 4.99 | 93 | 73 | 1765 | H(a): δ 0.73~1.62, m, 17H; H(b): δ 0.84~1.35, m, 5H; H(c): δ 1.20, s, 6H; H(d): δ 1.50~1.87, m, 6H | 40.5 |
| 7 | (cyclohexyl)-CH(CH$_3$)-OO-C(=O)-t-C$_{12}$H$_{25}$ (a); groups (d)(b)(c) | 4.06 | 90 | 70 | 1765 | H(a): δ 0.72~1.66, m, 25H; H(b): δ 0.82~1.33, m, 5H; H(c): δ 1.18, s, 6H; H(d): δ 1.52~1.85, m, 6H | 40.9 |

EXAMPLE 8

[Polymerization of vinyl chloride]

In an autoclave of stainless steel having an inner volume of 400 ml, 0.1 part by weight of polyvinyl alcohol was dissolved in 100 ml of deionized water. Then, the resultant solution and 0.07 part by weight as pure substance of the 1-cyclohexyl-1-methylethyl peroxy neo-decanoate (C-neo-decanoate) obtained in Example 3 added thereto were cooled to below −80° C. To the cooled mixture, 100 parts by weight of vinyl chloride monomer was added. The air in the empty space of the autoclave was thoroughly displaced with nitrogen gas and then the autoclave was airtightly stoppered. The autoclave was kept immersed in a constant temperature water bath maintained at 45° C. to effect polymerization of the monomer therein. The contents of the autoclave was stirred by rotating the autoclave at the rate of 32 r.p.m. in the water bath. The resultant polymerization mixture was cooled to expel the unaltered vinyl chloride monomer and obtain a white powder. The white powder was washed twice with 100 ml of water and then dried in a vacuum. From the weight of the white powder thus produced, the yield of the vinyl chloride polymer was found to be 84% and the average polymerization degree thereof to be 2,020. The vinyl chloride polymer was subjected to the following coloring test to determine thermal stability. It was also tested for odor. The results are shown in Table 2.

[Coloring Test and Odor]

A mixture consisting of 100 parts by weight of a given vinyl chloride polymer, 2.5 parts by weight of dibutyl tin malate, and 80 parts by weight of dioctyl phthalate as a plasticizer was kneaded with a rolling mill at 160° C. for 10 minutes to yield a sheet 1 mm in thickness. The sheet was visually examined as to degree of coloration. The sheet issuing from the rolling mill was examined for odor.

COMPARATIVE EXPERIMENTS 1 AND 2

Vinyl chloride monomer was polymerized by following the procedure of Example 8, except that CND and PMND were each used in a fixed amount of 0.07 part by weight in place of 0.07 part by weight of C-decanoate as a polymerization initiator. The results are shown in Table 2.

EXAMPLES 9 AND 10

Polymerization of vinyl chloride monomer was carried out by following the procedure of Example 8, except that the amount of C-decanoate added as a polymerization initiator and the polymerization temperature were varied. The results are shown in Table 2.

EXAMPLE 11

Polymerization of vinyl chloride monomer was carried out by following the procedure of Example 8, except that 0.03 part by weight of the 1-cyclohexyl-1-methylethyl peroxy pivalate (C-pivalate) obtained in Example 4 and 0.03 part by weight of t-butylperoxy neo-decanoate (BND) were used in place of 0.07 part by weight of the C-decanoate as a polymerization initiator. The results are shown in Table 2.

COMPARATIVE EXPERIMENT 3

For the purpose of comparison, polymerization of vinyl chloride monomer was carried out by following the procedure of Example 11, except that 0.03 part by weight of cumyl peroxy pivalate (CPV) and 0.03 part by weight of BND added thereto were used in place of 0.03 part by weight of the C-pivalate as a polymerization initiator. The results are shown in Table 2.

EXAMPLE 12

Polymerization of vinyl chloride monomer was carried out at a polymerization temperature by following the procedure of Example 8, except that 0.07 part by weight of the 1-cyclohexyl-1-methylethyl peroxy neo-nonanoate (C-neo-nonanoate) obtained in Example 6 was used in place of 0.07 part by weight of C-pivalate as a polymerization initiator. The results are shown in Table 2.

COMPARATIVE EXPERIMENT 4

For the purpose of comparison, polymerization of vinyl chloride monomer was carried out by following the procedure of Example 12, except that 0.07 part by weight of cumyl peroxy neo-nonanoate (CNH) was used in place of the C-neo-nonanoate as a polymerization initiator. The results are shown in Table 2.

EXAMPLE 13

[Copolymerization of vinyl chloride with vinyl acetate]

Polymerization was carried out by following the procedure of Example 8, except that 90 parts by weight of vinyl chloride monomer and 10 parts by weight of vinyl acetate monomer were used in place of 100 parts by weight of vinyl chloride monomer and the polymerization temperature was changed to 50° C. The results are shown in Table 2.

From the results, it is clear that the methods using polymerization initiators of the present invention produced polymers of satisfactory physical properties in higher yields than the methods using the conventional polymerization initiators for vinyl chloride monomer.

TABLE 2

|  | Example |  |  |  |  |  | Comparative Experiment |  |  |  |
|---|---|---|---|---|---|---|---|---|---|---|
|  | 8 | 9 | 10 | 11 | 12 | 13 | 1 | 2 | 3 | 4 |
| Vinyl chloride monomer (part by weight) | 100 | 100 | 100 | 100 | 100 | 90 | 100 | 100 | 100 | 100 |
| Vinyl acetate monomer (part by weight) | 0 | 0 | 0 | 0 | 0 | 10 | 0 | 0 | 0 | 0 |
| Polymerization temperature (°C.) | 45 | 40 | 50 | 52 | 45 | 50 | 45 | 45 | 52 | 45 |
| Amount added [1] |  |  |  |  |  |  |  |  |  |  |
| C-neodecanoate | 0.07 | 0.10 | 0.04 |  |  | 0.07 |  |  |  |  |
| C-pivalate |  |  |  | 0.03 |  |  |  |  |  |  |
| C-neononanoate |  |  |  |  | 0.07 |  |  |  |  |  |
| CND |  |  |  |  |  |  | 0.07 |  |  |  |
| PMND |  |  |  |  |  |  |  | 0.07 |  |  |
| BND |  |  |  | 0.03 |  |  |  |  | 0.03 |  |
| CNN |  |  |  |  |  |  |  |  |  | 0.07 |
| CPV |  |  |  |  |  |  |  |  | 0.03 |  |
| Yield (%) [2] | 84 | 83 | 82 | 83 | 86 | 75 | 77 | 79 | 79 | 80 |
| Average polymerization degree | 2020 | 2550 | 1500 | — | 2020 | — | 2000 | 2010 | — | 2010 |
| Coloration | none | none | none | none | none | none | none | none | none | none |
| Odor | none | none | none | none | none | none | [3] | [4] | [3] | [3] |

Note
[1] As pure substance (part by weight)
[2] Polymerization time - 8 hours
[3] Slight odor resembling that of acetophenone or phenol
[4] Smelled of terpene

EXAMPLE 14

[Polymerization of MMA]

In a four-neck flask having an inner volume of 500 ml and provided with a stirrer, a thermometer, a gas inlet tube, and a condenser, 0.1 part by weight of polyvinyl alcohol was dissolved in 200 ml of deionized water. Then, 200 parts by weight of methyl methacrylate, 0.5 part by weight of C-pivalate, and 0.1 part by weight of n-octyl mercaptan were added to the resultant solution. The air in the empty space of the flask was thoroughly displaced with nitrogen gas and the flask was heated at 60° C. for eight hours to effect polymerization of the monomer in the flask. The resultant polymerization mixture was cooled and filtered to obtain colorless, transparent beads of polymer. By determination of the residual monomer by means of gas chromatography, the conversion of polymerization was found to be 99.7%. By GPC, the number average molecular weight of the polymer was found to be 270,000 and the weight average molecular weight thereof to be 530,000.

COMPARATIVE EXPERIMENT 5

For the purpose of comparison, polymerization of MMA was carried out by following the procedure of Example 14, except that 0.07 part by weight of t-butyl peroxy pivalate was used in place of the C-pivalate as a polymerization initiator. As a result, the conversion of polymerization was found to be 90.3%. By GPC, the number average molecular weight was found to be 250,000 and the weight average molecular weight to be 515,000.

EXAMPLE 15

[Polymerization of MMA]

In a glass ampoule having an inner volume of 20 ml, 10 g of methyl methacrylate and 0.0046 g ($2 \times 10^{-5}$ mol) of the C-isobutyrate synthesized in Example 1 were placed. The ampoule was vacuumized, fused, and sealed. In a constant temperature oil bath, the monomer was polymerized at 80° C. for five hours and then further polymerized at 100° C. for two hours. The ampoule was opened and the resultant polymerization mixture was tested by gas chromatography to determine the residual monomer content. Consequently, the conversion of polymerization was found to be 96.6%. The polymer was odorless.

COMPARATIVE EXPERIMENTS 6 AND 7

Polymerization was carried out by following the procedure of Example 15, except that the various polymerization initiators indicated in Table 3 were individually used in an amount of $2 \times 10^{-5}$ mol in place of the C-isobutyrate. The results are shown in Table 3.

TABLE 3

| Comparative Experiment | Polymerization initiator | Conversion of polymerization (%) | Odor of polymer |
|---|---|---|---|
| 6 | BPO | 89.7 | none |
| 7 | PMO | 91.5 | odor of terpene |

EXAMPLE 16

[Copolymerization of MMA]

A mixture consisting of 99 parts by weight of methyl methacrylate, 1 part by weight of methyl acrylate, 0.05 part by weight of C-pivalate, 0.1 part by weight of n-dodecyl mercaptan, and 0.1 part by weight of triphenyl phosphine was poured in a mold prepared by the use of two glass sheets, heated in a constant temperature bath at 50° C. for five hours, then heated to 80° C., and kept at this temperature for two hours to complete polymerization. The produced polymer was cooled and removed from the glass sheet. Consequently, a transparent sheet 3 mm thickness was obtained. This sheet was perfectly free from color and odor.

COMPARATIVE EXPERIMENT 8

For the purpose of comparison, polymerization was carried out by following the procedure of Example 6, except that 0.05 part by weight of paramenthane peroxy pivalate (PMPV) was used in place of the C-pivalate as a polymerization initiator. The produced sheet was colorless. It smelled of terpene.

EXAMPLE 17

In a glass ampoule having an inner volume of 20 ml, 9.9 g of methyl methacrylate, 0.1 g of butyl acrylate, 0.02 g of n-dodecyl mercaptan, and 0.0057 g ($2 \times 10^{-5}$ mol) of the C-octoate synthesized in Example 2 were placed. The ampoule was vacuumized, fused, and airtightly sealed. The ampoule was then left standing in a constant temperature oil bath at 90° C. for seven hours to polymerize the monomer therein. The produced polymer was removed from the ampoule. The conversion of polymerization was found to be 97.4%.

COMPARATIVE EXPERIMENT 9

Polymerization was carried out by following the procedure of Example 17, except that 0.0045 g ($2 \times 10^{-5}$ mol) of t-butyl peroxy octoate (t-BO) was used in place of the C-octoate. As a result, the conversion of polymerization was found to be 90.1%.

EXAMPLE 18

[Polymerization of styrene]

In an autoclave of stainless steel having an inner volume of 500 ml, 0.1 g of polyvinyl alcohol was dissolved in 200 ml of deionized water. To the resultant solution were added 200 g of styrene and 0.228 g (0.001 mol) of the C-isobutyrate synthesized in Example 1. The air in the empty space of the autoclave was thoroughly displaced with nitrogen gas and then the autoclave was airtightly stoppered. The autoclave was heated in a constant temperature oil bath at 100° C. for 10 hours to polymerize the monomer. The monomer inside the autoclave was stirred by rotating the autoclave at the rate of 32 r.p.m. in the oil bath. The resultant polymer was cooled, thrown into methanol to be reprecipitated, separated by filtration, and dried. Based on the weight of the produced white powder, the conversion of polymerization was found to be 78.1%. This polymer was odorless.

COMPARATIVE EXPERIMENTS 10 AND 11

Polymerization was carried out by following the procedure of Example 18, except that 0.001 mol of various polymerization initiators shown in Table 4 were individually used in place of the C-isobutyrate. The results are shown in Table 4.

TABLE 4

| Comparative Experiment | Polymerization initiator | Conversion of polymerization (%) | Odor of polymer |
|---|---|---|---|
| 10 | BPO | 54.0 | none |
| 11 | PEO | 72.3 | odor of terpene |

EXAMPLES 19 AND 20 AND COMPARATIVE EXPERIMENTS 12 AND 13

In the same apparatus as used in Example 18, 0.1 g of polyvinyl alcohol was dissolved in 200 ml of deionized water. To the resultant solution were added 200 g of styrene and $4 \times 10^{-4}$ mol of one of the polymerization initiators indicated in Table 5. In a constant temperature oil bath, the monomer in the autoclave was continuously heated so as to elevate the temperature at a fixed rate from 80° C. to 120° C. over a period of 10 hours to polymerize the monomer. Thereafter, polystyrene was produced by following the procedure of Example 18.

The results are shown in Table 5.

TABLE 5

| | Polymerization initiator | Conversion of polymerization (%) | Odor of polymer |
|---|---|---|---|
| Example | | | |
| 19 | C-octoate [1] DBM [2] | 98.7 | none |
| 20 | C-octoate [1] TBZ [3] | 99.0 | " |
| Comparative Experiment | | | |
| 12 | BPO [4] DBM [2] | 91.8 | " |
| 13 | t-BO [5] TBZ [3] | 93.1 | " |

[1] Synthesized in Example 2
[2] 1,1-Bis(t-butylperoxy)-3,3,5-trimethyl cyclohexane
[3] t-Butylperoxy benzoate
[4] Benzoyl peroxide
[5] t-Butyl peroxy octoate

EXAMPLE 21

[Copolymerization of styrene and acrylonitrile]

In the same apparatus as used in Example 18, 0.1 g of polyvinyl alcohol was dissolved in 200 ml of deionized water. To the resultant solution were added 140 g of styrene, 60 g of acrylonitrile, and 0.456 g (0.002 mol) of the C-isobutyrate synthesized in Example 1. Thereafter, the procedure of Example 18 was followed. The conversion of polymerization was found to be 90.6%. The produced polymer was odorless.

COMPARATIVE EXPERIMENT 14

Polymerization was carried out by following the procedure of Example 21, except that 0.488 g (0.002 mol) of BPO was used in place of the C-isobutyrate. The conversion of polymerization was found to be 81.7%.

EXAMPLE 22

[Polymerization of vinyl acetate]

One hundred (100) parts by weight of vinyl acetate monomer was dissolved in 50 parts by weight of methanol. The resultant monomer mixture was simultaneously refluxed and stirred and then, by the addition of 0.05 part by weight of C-pivalate, polymerized for five hours. As a result, polyvinyl acetate having a polymerization degree of 741 was obtained. The conversion of polymerization was found to be 69.8%. The produced polymer was perfectly colorless.

COMPARATIVE EXPERIMENT 15

For the purpose of comparison, polymerization of vinyl acetate was carried out by following the procedure of Example 22, except that 0.10 part by weight of AIBN was used in place of C-pivalate as a polymerization initiator. As a result, polyvinyl acetate having a polymerization degree of 765 was obtained. The conversion of polymerization was found to be 70.3%. The produced polymer was light yellow.

From the results indicated above, it is clear that in the polymerization and copolymerization of methyl methacrylate, styrene, and vinyl acetate, the methods using polymerization initiators conforming to the present invention produced polymers of better quality than the methods using the conventional polymerization initiators.

EXAMPLE 23

[Curing of unsaturated polyester resin]

In a beaker having an inner volume of 50 ml, 50 g of an unsaturated polyester resin (produced by Nippon Shokubai Kagaku Kogyo Co., Ltd. and marketed as "Eporack G110A1") and 0.25 g of the C-isobutyrate synthesized in Example 1 were thoroughly mixed by the use of a glass bar until a homogeneous solution was formed. The resultant resin solution was placed to a depth of 100 mm in a double-wall test tube 18 mm in diameter. The test tube was placed in a constant temperature bath set at 80° C. The sample gelling time (time required for the test tube temperature to rise to between 65° C. and 85° C. with the test tube set in an 80° C. constant temperature bath) and the minimum curing time (time required for the test tube temperature to rise from 65° C. to the maximum temperature) were checked and found to be 5.6 minutes and 7.2 minutes, respectively.

COMPARATIVE EXPERIMENTS 16 AND 17

The curing of an unsaturated polyester resin was carried out by following the procedure of Example 9, except that 0.25 g of a one of the curing agents indicated in Table 6 was used in place of the C-isobutyrate of Example 23. The results are shown in Table 6.

TABLE 6

| Comparative Experiment | Curing agent | Gelling time (min.) | Minimum curing time (min.) | Odor of cured produced |
|---|---|---|---|---|
| 9 | BPO | 6.8 | 8.4 | none |
| 10 | PEO | 6.1 | 7.9 | odor of terpene |

What is claimed is:

1. A 1-cyclohexyl-1-methylethyl peroxy ester represented by the formula:

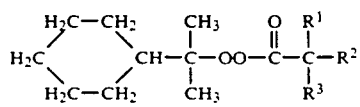

wherein $R^1$ stands for one member selected from the group consisting of H and alkyl groups and $R^2$ and $R^3$ independently stand for an alkyl group, provided that $R^2$ and $R^3$ each stand for an alkyl group of 1 to 5 carbon atoms and the sum of the carbon atoms of $R^2$ and $R^3$ is in the range of from 2 to 6 where $R^1$ is H and $R^1$, $R^2$, and $R^3$ each stand for an alkyl group of 1 to 9 carbon atoms and the sum of the carbon atoms of $R^1$, $R^2$, and $R^3$ is in the range of from 3 to 11 where $R^1$ is an alkyl group.

2. A 1-cyclohexyl-1-methylethyl peroxy ester according to claim 1, wherein $R^1$ is H.

3. A 1-cyclohexyl-1-methylethyl peroxy ester according to claim 2, which is one member selected from the group consisting of 1-cyclohexyl-1-methylethyl peroxy isobutyrate and 1-cyclohexyl-1-methylethyl peroxy octoate.

4. A 1-cyclohexyl-1-methylethyl peroxy ester according to claim 1, wherein $R^1$ is an alkyl group.

5. A 1-cyclohexyl-1-methylethyl peroxy ester according to claim 4, which is one member selected from the group consisting of 1-cyclohexyl-1-methylethyl peroxy pivalate, 1-cyclohexyl-1-methylethyl peroxy neo-hexanoate, 1-cyclohexyl-1-methylethyl peroxy neo-nonanoate, 1-cyclohexyl-1-methylethyl peroxy neo-decanoate, and 1-cyclohexyl-1-methylethyl peroxy neo-tridecanoate.

* * * * *